United States Patent
Ueyama et al.

(10) Patent No.: US 10,113,859 B2
(45) Date of Patent: Oct. 30, 2018

(54) IMAGING APPARATUS AND IMAGING METHOD

(71) Applicant: SCREEN HOLDINGS CO., LTD., Kyoto (JP)

(72) Inventors: Kenji Ueyama, Kyoto (JP); Kumiko Fukue, Kyoto (JP)

(73) Assignee: Screen Holdings Co., Ltd., Kyoto (JP)

( * ) Notice: Subject to any disclaimer, the term of this patent is extended or adjusted under 35 U.S.C. 154(b) by 0 days.

(21) Appl. No.: 15/264,019

(22) Filed: Sep. 13, 2016

(65) Prior Publication Data

US 2017/0167847 A1    Jun. 15, 2017

(30) Foreign Application Priority Data

Dec. 11, 2015 (JP) ................................ 2015-241807

(51) Int. Cl.
```
G01B 9/02      (2006.01)
G01B 11/02     (2006.01)
G01N 33/483    (2006.01)
G02B 27/00     (2006.01)
```

(52) U.S. Cl.
CPC ..... *G01B 9/02091* (2013.01); *G01B 9/02001* (2013.01); *G01B 9/02044* (2013.01); *G01B 9/02059* (2013.01); *G01N 33/4833* (2013.01); *G02B 27/0018* (2013.01)

(58) Field of Classification Search
CPC ............ G01B 9/02004; G01B 9/02059; G01B 9/02091; G02B 27/0018; G02B 27/0988; G02B 5/201; G02B 26/023
See application file for complete search history.

(56) References Cited

U.S. PATENT DOCUMENTS

| 5,327,219 A | 7/1994 | Steimle et al. |
| 2008/0285043 A1* | 11/2008 | Fercher ................. A61B 3/102 356/451 |
| 2011/0058175 A1 | 3/2011 | Suehira |

(Continued)

FOREIGN PATENT DOCUMENTS

| JP | 2010-038910 A | 2/2010 |
| JP | 5688185 B2 | 3/2015 |
| WO | 2013/136476 A1 | 9/2013 |

OTHER PUBLICATIONS

Extended European Search Report issued in corresponding EP Patent Application No. 16186551.4, dated Mar. 3, 2017.

*Primary Examiner* — Michael A Lyons
(74) *Attorney, Agent, or Firm* — McDermott Will & Emery LLP

(57) ABSTRACT

An OCT imaging technique capable of suppressing image noise due to reflection on a wall surface of a carrier for carrying an imaging object by a simple configuration is provided. A light regulating member 28 having a transmission pattern where the high transmission parts P1 and the low transmission parts P2 are alternately arranged is placed on a side opposite to the spheroid Sp (imaging object) across the objective lens 27. The transmission pattern is rotationally symmetric with respect to an optical axis AX of the objective lens 27 and a point located at a position point-symmetric with an arbitrary point in the high transmission part with respect to a point where the optical axis of the objective lens intersects with the light regulating surface is included in the low transmission part.

11 Claims, 9 Drawing Sheets

(56) References Cited

U.S. PATENT DOCUMENTS

| | | | |
|---|---|---|---|
| 2013/0027714 A1* | 1/2013 | Yoshii | H01S 5/143 356/497 |
| 2013/0342847 A1 | 12/2013 | Karr | |
| 2014/0247426 A1 | 9/2014 | Suehira | |
| 2015/0092196 A1* | 4/2015 | Osawa | G01B 9/02025 356/479 |
| 2016/0097632 A1* | 4/2016 | Sumiya | G01B 9/02091 356/479 |
| 2016/0265899 A1* | 9/2016 | Minemura | G01B 9/02064 |

\* cited by examiner

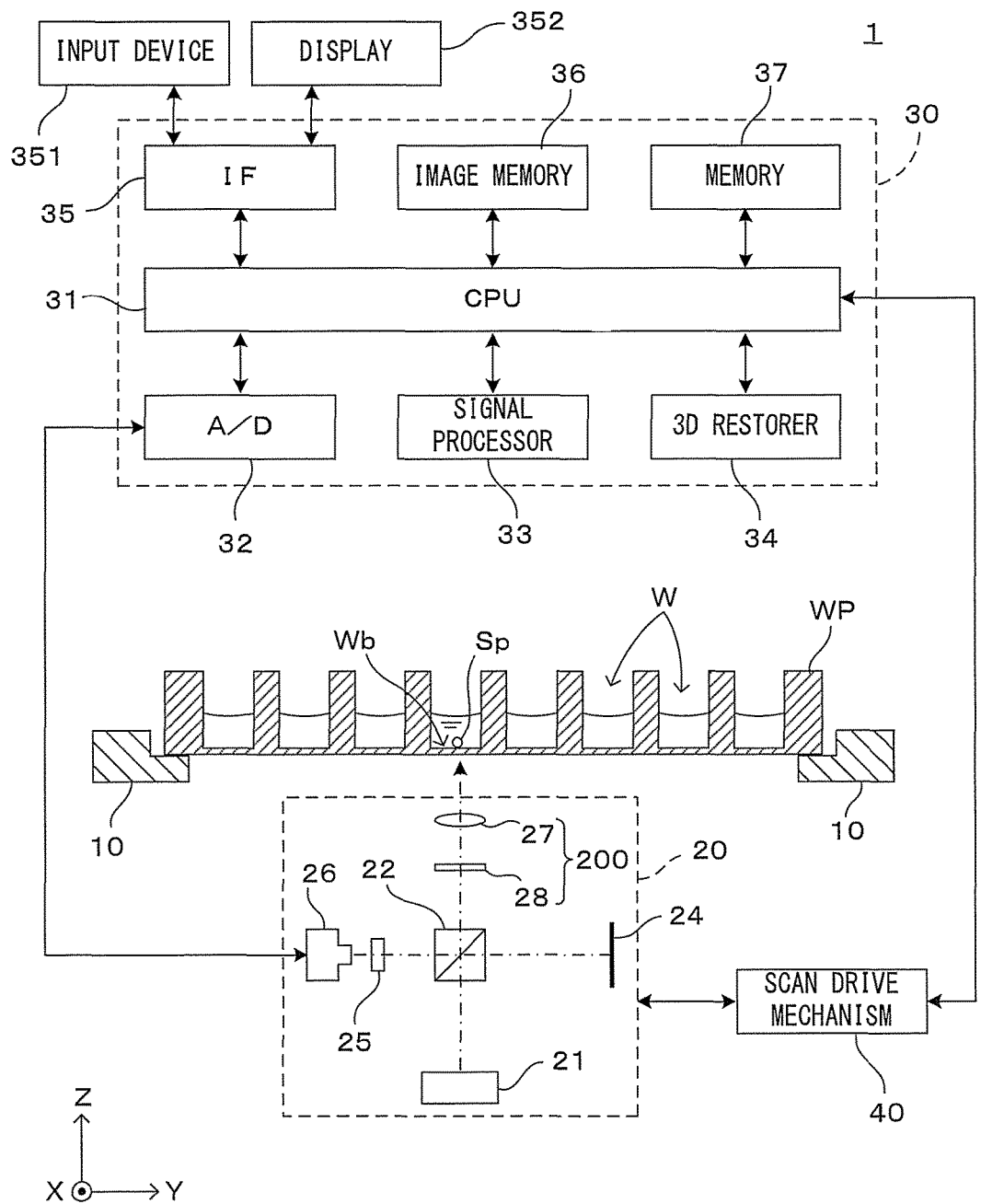
F I G. 1

IMAGING APPARATUS AND IMAGING METHOD

CROSS REFERENCE TO RELATED APPLICATION

The disclosure of Japanese Patent Application No. 2015-241807 filed on Dec. 11, 2015 including specification, drawings and claims is incorporated herein by reference in its entirety.

BACKGROUND OF THE INVENTION

1. Field of the Invention

This invention relates to a technique for imaging by detecting an interference light component of reflected light from an imaging object and reference light and particularly to a technique for imaging an imaging object carried in a carrier having optical transparency.

2. Description of the Related Art

In technical fields of medicine and biochemistry, samples carried in an appropriate carrier such as cells and microorganisms cultured in a container are observed. Techniques for imaging cells and the like using a microscope or the like are proposed as methods for observation without affecting the cells and the like to be observed. One of such techniques utilizes an optical coherence tomography technique. In this technique, low-coherence light emitted from a light source is caused to be incident as illumination light on an imaging object and interference light of reflected light (signal light) from the imaging object and reference light having a known optical path length is detected, whereby an intensity distribution in a depth direction of the reflected light from the imaging object is obtained for tomographic imaging. In this technique, reflected lights from a plurality of interfaces of the imaging object may be superimposed, thereby generating ghost-like image noise called self-correlation noise.

To deal with this problem, a shutter is provided in each of an optical path of return light from an object to be inspected and that of reference light, for example, in a technique described in JP 2010-038910A. By opening and closing these shutters if necessary, each of the return light and the reference light is singly detected and a self-correlation component of each is obtained. Further, a shutter mechanism for shutting off reflected light from an object is disclosed, for example, in International Publication No. 2013/136476, and this mechanism is described to remove image noise by software. This is supposed to cancel noise due to a self-correlation component of reference light.

If the cells and the like described above are an imaging object, imaging may be performed via a wall surface (e.g. bottom surface) of a carrier having optical transparency. In such a case, reflected light from the carrier wall surface is superimposed on a signal light, thereby acting similarly to reference light and image noise like a ghost image of the imaging object may appear at a depth different from the original one according to a distance between the wall surface and the imaging object. For such image noise, a process for removing the image noise ex-post facto is necessary in the above conventional technique and it cannot be dealt with in real time. Further, the reflected light from the wall surface and reflected light from the imaging object cannot be separated by opening and closing the shutters. Further, the above conventional technique has a complicated configuration in mechanism and operation such as because an optical system requires a movable mechanism and signal detection is necessary in each of an open state and a closed state of the shutter. Thus, it is desired to establish a technique capable of suppressing image noise due to reflected light from a carrier wall surface without complicating a configuration.

SUMMARY OF THE INVENTION

This invention was developed in view of the above problem and an object thereof is to provide a technique capable of suppressing image noise due to reflection on a wall surface of a carrier by a simple configuration in a technique for imaging an imaging object utilizing the interference of reflected light from the imaging object and reference light.

One aspect of this invention is directed to an imaging apparatus for tomographically imaging an imaging object carried in a carrier having an optically transparent wall surface and, to achieve the above object, the imaging apparatus comprises a light source which emits low-coherence light, a detector which causes one branch light obtained by dividing light from the light source into a plurality of optical paths to be incident as illumination light on the imaging object via an object optical system, detects interference light generated by an interference of signal light reflected from the imaging object and incident on the object optical system and reference light based on another branch light and outputs an interference signal corresponding to detected interference light, and a signal processor which obtains a reflected light intensity distribution of the imaging object along an incident direction of the illumination light based on the interference signal.

Further, another aspect of this invention is directed to an imaging method for tomographically imaging an imaging object carried in a carrier having an optically transparent wall surface and, to achieve the above object, the imaging method comprises dividing low-coherence light emitted from the light source into a plurality of optical paths, causing one branch light to be incident as illumination light on the imaging object via an object optical system, detecting interference light generated by the interference of signal light reflected from the imaging object and incident on the object optical system and reference light based on another branched light, and obtaining a reflected light intensity distribution of the imaging object along an incident direction of the illumination light based on the detected interference light.

Here, the object optical system includes an objective lens and a light regulator, the objective lens is arranged to face the wall surface, converges the illumination light to the imaging object via the wall surface and collects the signal light from the imaging object emitted via the wall surface, the light regulator is arranged on an optical path of the illumination light on a side opposite to the imaging object across the objective lens and has a light regulating surface formed with a transmission pattern in which a high transmission part for transmitting the illumination light at a relatively high transmittance and a low transmission part having a lower transmittance to the illumination light than the high transmission parts are regularly arranged, and the transmission pattern is rotationally symmetric with respect to an optical axis of the objective lens and a point located at a position point-symmetric with an arbitrary point in the high transmission part with respect to a point where the optical axis of the objective lens intersects with the light regulating surface is included in the low transmission part.

In the invention thus configured, the illumination light is incident on the imaging object via the light regulating surface of the light regulator, the objective lens and the wall surface of the carrier. Light incident on the high transmission part of the light regulating surface out of the illumination light passes through the light regulating surface and reaches the wall surface and is partially reflected by the wall surface. Regularly reflected light by the wall surface reaches the light regulating surface again via the objective lens.

There is considered an optical path of light incident on a reflecting surface near an object-side focal plane via the light regulating surface and the objective lens, regularly reflected by this reflecting surface and returning via the objective lens and the light regulating surface. Here, out of this optical path, an optical path from the light source to the incidence on the reflecting surface is called an incident optical path and that of the light reflected by the reflecting surface is called a reflection optical path. At this time, since the transmission pattern of the light regulating surface has the above symmetry, light passing though the high transmission part of the light regulating surface at the incident optical path passes through the low transmission part of the light regulating surface at the reflection optical path. On the other hand, light passing through the high transmission part of the light regulating surface as regularly reflected light at the reflection optical path is limited to light having passed through the low transmission part of the light regulating surface at the incident optical path.

As just described, the low transmission part of the light regulating surface is invariably present on the optical path of light emitted from the light source, incident on the reflecting surface via the object optical system, regularly reflected by the reflecting surface and passing through the object optical system. Thus, the light passing along this optical path is largely attenuated. On the other hand, it is possible to use scattered light scattered by the imaging object as the signal light, and the scattered light is emitted in various directions. Accordingly, the signal light passing through the light regulating surface is only subjected to attenuation corresponding to transmittance and area ratios between the high transmission part and the low transmission part. Thus, a ratio of the regularly reflected light to the signal light incident on the detector via the object optical system is drastically reduced. In other words, an S/N ratio (Signal-to-Noise Ratio) of the signal light to the regularly reflected light increases.

When the wall surface of the carrier is near a focus position of the objective lens, the regularly reflected light thereby acts as pseudo reference light and interferes with the signal light, whereby ghost-like image noise can be generated. Since the regularly reflected light incident on the detector is largely reduced in the invention, the generation of such image noise can be effectively suppressed.

The light regulator of the invention has a function of partially regulating passing light. An aperture stop is generally used for this purpose. However, a special transmission pattern having the above symmetry is necessary to selectively regulate the regularly reflected light and prevent a NA (Numerical Aperture) reduction of the object optical system leading to a reduction of resolution.

As described above, according to the invention, it is possible to drastically reduce image noise generated by the action of regularly reflected light from a wall surface of the carrier as if it were reference light in imaging via the wall surface.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

BRIEF DESCRIPTION OF THE DRAWINGS

FIG. 1 is a drawing which shows the image processing apparatus as an embodiment of the imaging apparatus according to the invention.

DETAILED DESCRIPTION OF THE PREFERRED EMBODIMENTS

Figure 2A:
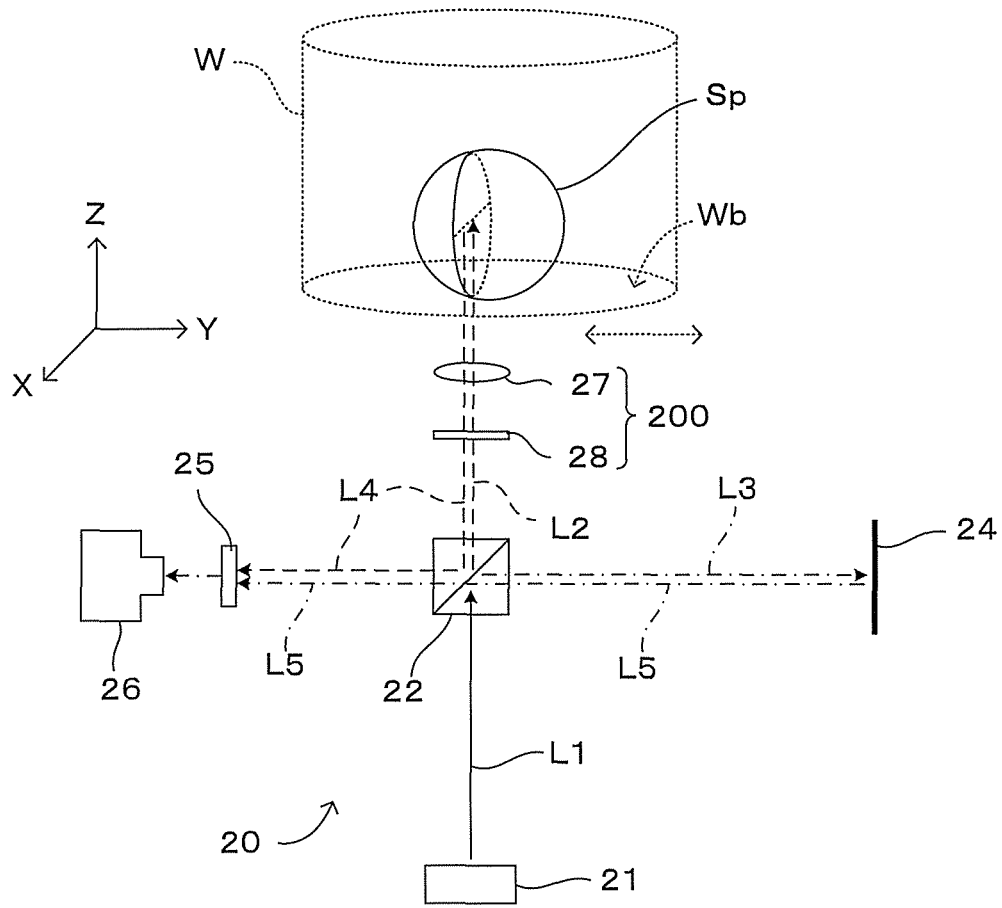
FIGS. 2A and 2B are drawings for describing the principle of imaging in this image processing apparatus.

FIG. 1 is a drawing which shows the image processing apparatus as an embodiment of the imaging apparatus according to the invention. The image processing apparatus 1 tomographically images a spheroid (cell aggregate) cultured in liquid (culture liquid, for example), processes the obtained image and generates a stereoscopic image of the spheroid. For unified presentation of the directions in drawings, the XYZ orthogonal coordinate axes are established as shown in FIG. 1. The XY plane is a horizontal surface. The Z axis represents the vertical axis, in more detail, the (−Z) direction represents the vertically downward direction.

The image processing apparatus 1 comprises a holder 10. The holder 10 holds in an approximately horizontal posture a well plate (which is also called a "micro-plate") WP, in which a number of dents (wells) W which can hold a liquid at the top surface of a plate-like member, in such a manner that the openings of the wells W are directed toward above. A predetermined amount of an appropriate culture liquid is poured in each well W of the well plate WP in advance, and a spheroid Sp is cultured in the liquid at the bottom surface Wb of the well W. Although FIG. 1 shows the spheroids Sp only in some wells W, the spheroid Sp is cultured in each one of the wells W.

An imaging unit 20 is disposed below the well plate WP which is held by the holder 10. The imaging unit 20 is an optical coherence tomography (OCT) apparatus capable of imaging tomographic images of a target object (imaging object) in a non-contact non-destructive (non-invasive) manner. The imaging unit 20 which is an OCT apparatus comprises a light source 21 which emits illumination light for a target object, a beam splitter 22 which splits light from the light source 21, an object optical system 200, a reference mirror 24, a spectroscope 25 and a photo-detector 26.

Further, the image processing apparatus 1 comprises a control unit 30 which controls operations of the apparatus and a scan drive mechanism 40 which drives movable parts of the imaging unit 20. The control unit 30 comprises a CPU (Central Processing Unit) 31, an A/D convertor 32, a signal processor 33, a 3D restoration section 34, an interface (IF) section 35, an image memory 36 and a memory 37.

The CPU 31 governs operations of the entire apparatus by executing a predetermined control program and the control program executed by the CPU 31 and data which are generated during processing are saved in the memory 37. The A/D convertor 32 converts a signal which the photo-detector 26 of the imaging unit 20 outputs in accordance with the amount of received light into digital image data. The signal processor 33 performs image processing described later based upon a digital data outputted from the A/D converter 32, thereby generates a tomographic image of the imaging object. Based upon image data of a plurality of tomographic images, the 3D restoration section 34 generates a stereoscopic image (3D image) of the imaged cell aggregate. The image memory 36 saves the image data of the tomographic images generated by the signal processor 33 and the image data of the stereoscopic image generated by the 3D restoration section 34.

The interface section 35 realizes communication between the image processing apparatus 1 and outside. More specifically, the interface section 35 has a function of communicating with external equipment, and a user interface function of accepting manipulation by a user and informing the user of various types of information. For this purpose, an input device 351 and a display section 352 are connected to the interface section 35. The input device 351 is for instance a key board, a mouse, a touch panel or the like which can accept manipulation and entry concerning selection of the functions of the apparatus, setting of operating conditions, etc. The display section 352 comprises a liquid crystal display for example which shows various types of processing results such as the tomographic images imaged by the imaging unit 20 and the stereoscopic image generated by the 3D restoration section 34.

Further, the scan drive mechanism 40 makes the imaging unit 20 scan and move in accordance with a control command given from the CPU 31. As described next, the tomographic images of the cell aggregate which is the imaging object are obtained owing to combination of scan moving of the imaging unit 20 executed by the scan drive mechanism 40 and detection of the amount of the received light by the photo-detector 26.

Figure 2B:
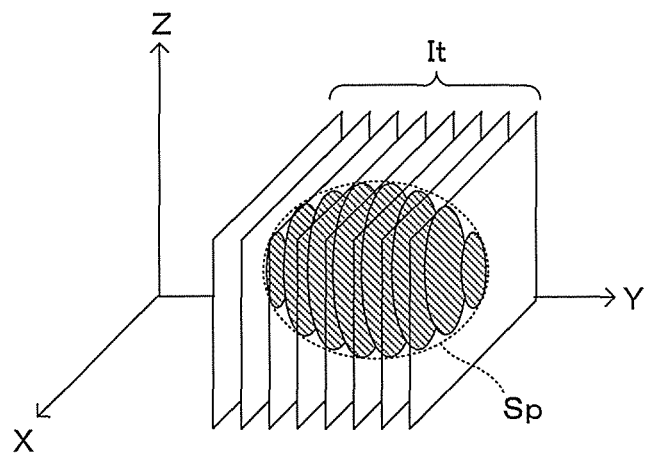

FIGS. 2A and 2B are drawings for describing the principle of imaging in this image processing apparatus. More specifically, FIG. 2A is a drawing which shows optical paths inside the imaging unit 20, and FIG. 2B is a schematic drawing which shows tomographic imaging of a spheroid. As described earlier, the imaging unit 20 works as an optical coherence tomography (OCT) apparatus.

In the imaging unit 20, from the light source 21 which includes a light emitting element such as a light emitting diode or a super luminescent diode (SLD) for instance, a low-coherence light beam L1 containing a wide-range wavelength components is emitted. The light beam L1 impinges upon the beam splitter 22, and some light L2 indicated by the dotted-line arrow propagates toward the well W, and some light L3 indicated by the arrow of long dashed short dashed line propagates toward the reference mirror 24.

The light L2 propagating toward the well W is incident on the well W by way of the object optical system 200. More specifically, the light L2 emitted from the beam splitter 22 is incident on the well bottom surface Wb via a light regulating member 28 and an objective lens 27 provided in the object optical system 200. As described in detail later, the light regulating member 28 has a function of enhancing an S/N (Signal-to-Noise) ratio of the light incident on the photo-detector 26 by partially shielding the light propagating from the beam splitter 22 toward the well W and the light propagating from the well W toward the beam splitter 22. Further, the objective lens 27 has a function of converging the light L2 propagating from the beam splitter 22 toward the well W to the imaging object in the well W (spheroid Sp in this case) and a function of collecting the reflected light emitted from the imaging object and causing it to propagate toward the beam splitter 22.

An optical axis of the objective lens 27 is parallel to a vertical direction and, hence, perpendicular to the flat well bottom surface Wb. Further, an incident direction of illumination light on the objective lens 27 is parallel to the optical axis. The arrangement of the object optical system 200 is determined such that a center of the illumination light coincides with the optical axis.

The light L2 is reflected at the surface of the spheroid Sp unless the spheroid Sp transmits the light beam L2. On the other hand, when the spheroid Sp has a property of transmitting the light beam L2 to a certain extent, the light beam L2 propagates into inside the spheroid Sp and is reflected by a structure element which is inside the spheroid. When the near infrared rays for instance are used as the light beam L2, it is possible to allow the incident light to reach even inside the spheroid Sp. The reflected light from the spheroid Sp is irradiated as scattered light in various directions. Out of that, light L4 irradiated within a light collection range of the objective lens 27 is collected by the objective lens 27 and sent to the beam splitter 22.

The reflected light L4 reflected by a surface or an internal reflecting surface of the spheroid Sp and reference light L5 reflected by the reference mirror 24 are incident on the photo-detector 26 via the beam splitter 22. At this time, interference due to a phase difference between the reflected light L4 and the reference light L5 occurs, but an optical spectrum of interference light differs depending on a depth of the reflecting surface. That is, the optical spectrum of the interference light has information on a depth direction of the imaging object. Thus, a reflected light intensity distribution in the depth direction of the imaging object can be obtained by spectrally diffracting the interference light at each wavelength to detect a light quantity and Fourier transforming a detected interference signal. An OCT imaging technique based on such a principle is called Fourier domain OCT (FD-OCT).

The imaging unit 20 of this embodiment is provided with a spectroscope 25 on an optical path of the interference light from the beam splitter 22 to the photo-detector 26. A spectroscope utilizing a prism, a spectroscope utilizing a diffraction grating and the like can be, for example, used as the spectroscope 25. The interference light is spectrally diffracted for each wavelength component and received by the photo-detector 26.

By Fourier transforming the interference signal output from the photo-detector 26 according to the interference light detected by the photo-detector 26, the reflected light intensity distribution in the depth direction, i.e. in the Z direction at an incident position of the light beam L2 on the spheroid Sp is obtained. By scanning the light beam L2 incident on the well W in the X direction, a reflected light intensity distribution in a plane parallel to an XZ plane can be obtained and a tomographic image of the spheroid Sp having a cross-section on this plane can be generated from that result.

As indicated by the arrow A2, the relative position of the imaging unit 20 to the well W is changed along the Y direction over multiple steps, and a tomographic image is imaged for every change. As a result, as shown in FIG. 2B, a number of tomographic images It of the spheroid Sp are obtained along cross-sectional surfaces which are parallel to the XZ plane. As the scan pitch in the Y direction is reduced, it is possible to obtain image data with sufficient resolution to grasp the stereoscopic structure of the spheroid Sp. Scan movements of the respective parts above in the imaging unit 20 are realized as the scan drive mechanism 40 operates after receiving a control command from the CPU 31.

Note that the imaging unit 20 causes the interference of the reflected light from the imaging object and the reference light from the reference mirror 24 using the beam splitter 22 in the above. However, besides this, there is also an OCT apparatus for causing the interference of reflected light and reference light using an optical fiber coupler. As described later, the OCT apparatus of such a type can be applied also in this embodiment.

Figure 3:
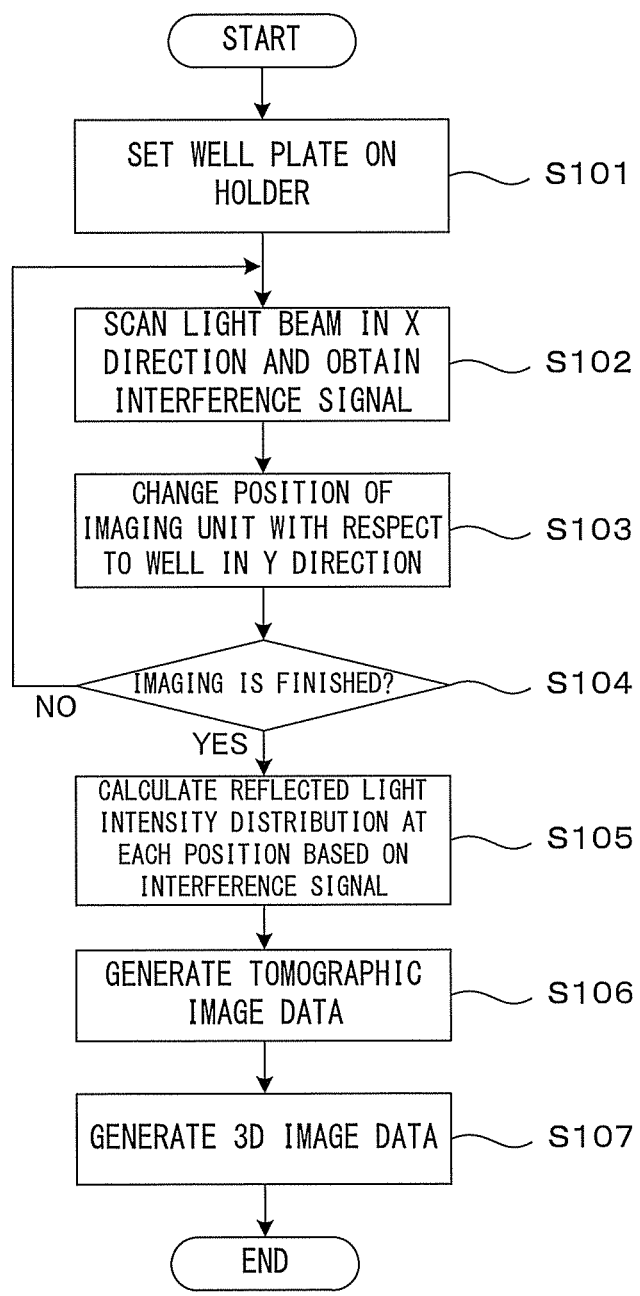
FIG. 3 is a flow chart showing the operation of this image processing apparatus.

FIG. 3 is a flow chart showing the operation of this image processing apparatus. This operation is realized by the CPU 31 executing the control program written in the memory 37 in advance to control each part of the apparatus and cause each part to perform a predetermined operation. First, the well plate WP carrying spheroids Sp to be imaged together with the culture liquid is set on the holder 10 by a user or a conveyor robot (Step S101). The CPU 31 performs the tomographic imaging of the spheroids Sp in the well W as the imaging object by controlling the imaging unit 20 and the scan drive mechanism 40 (Step S102 to S104).

More specifically, the incident position on the well W is changed in the X direction by scanning the light beam L2, the interference light at each position is detected by the photo-detector 26 and an interference signal in a cross-section parallel to the XZ plane is obtained (Step S102). The interference signal converted into digital data is stored and saved in the memory 37. The above process is repeated until the imaging of the entire well W is finished (Step S104) while the scan drive mechanism 40 changes a relative position of the imaging unit 20 with respect to the well W at a predetermined interval in the Y direction (Step S103).

Based on the interference signal obtained at each position of the well W in this way, the signal processor 33 calculates a reflected light intensity distribution in the depth direction at each position (Step S105). Then, the signal processor 33 generates tomographic image data representing a tomographic image in the well W in one cross-section parallel to the XZ plane from the reflected light intensity distribution at each position in the X direction (Step S106). Similarly, tomographic image data is generated at each position in the Y direction. The generated tomographic image data is stored and saved in the image memory 36.

Based on the tomographic image data thus obtained, the 3D restorer 34 generates 3D image data corresponding to a stereoscopic image of the spheroid Sp (Step S107). Specifically, it is possible to obtain 3D image data, for example, by interpolation in the Y direction of tomographic image data discretely obtained in the Y direction. A technique for generating 3D image data from tomographic image data is not described in detail since it is already put to practical use.

Next, the significance of providing the light regulating member 28 in the object optical system 200 provided between the beam splitter 22 and the well bottom surface Wb is described. First, a problem in a generally configured OCT apparatus including no light regulating member is described with reference to FIGS. 4A to 4C. To facilitate understanding, constituent components same as or corresponding to those of the image processing apparatus 1 described above are denoted by the same reference signs and not described.

In the OCT apparatus, scattered light caused by scattering illumination light by an imaging object (spheroid Sp) is used as a signal light (light L4 in FIG. 2A) and an interference light component of this signal light and reference light (light L5 in FIG. 2A) emitted from the reference mirror 24 is detected to obtain a reflected light intensity distribution from the imaging object. An optical path length of the reference light is selected to be approximately equivalent to that of reflected light from the imaging object. In this way, reflected light from an interface of the imaging object near a virtual base surface (reference base surface) assumed at a position equivalent to the reference mirror 24 in optical path length interferes with the reference light. The presence of the interface in the imaging object is detected from this interference light.

In the case of imaging the spheroid Sp in the well W via the well bottom surface Wb having optical transparency, a part of the illumination light to be incident on the spheroid Sp as the imaging object is reflected by the well bottom surface Wb. On the well bottom surface Wb, reflection can occur both on a well inner bottom surface on a side in contact with the culture medium carried in the well W and on a well outer bottom surface on a side where the illumination light is incident. In this specification, a concept including both of these is called the "well bottom surface Wb". Particularly, a smoothly finished surface generates strong regularly reflected light.

Figure 4A:
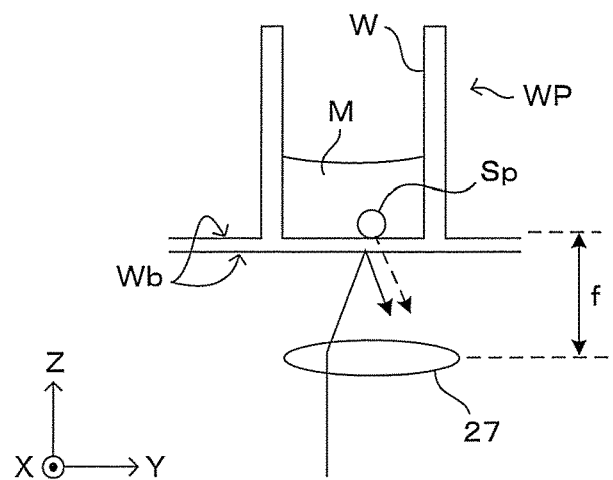
FIGS. 4A to 4C are diagrams showing the problem of the configuration including no light regulating member.
Figure 4B:
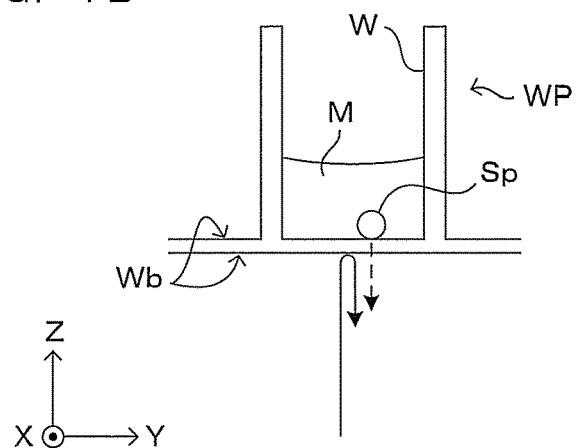
Figure 4C:
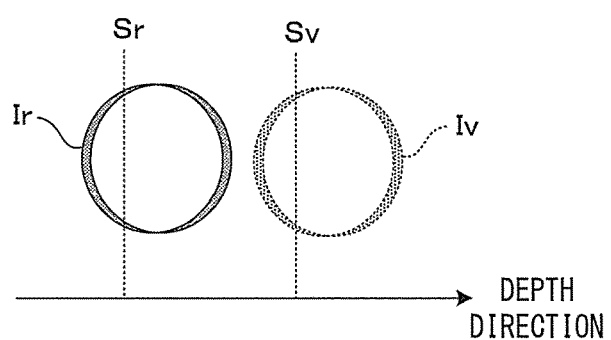

FIGS. 4A to 4C are diagrams showing the problem of the configuration including no light regulating member. FIG. 4A shows an example of a configuration provided with the objective lens 27. As shown in FIG. 4A, in the configuration provided with the objective lens 27 to obtain a high magnification image, a focal point (object-side focal point) of the objective lens 27 is substantially adjusted to the spheroid Sp to converge illumination light to the spheroid Sp and efficiently collect reflected light irradiated from the spheroid Sp. Specifically, a distance between the objective lens 27 and the spheroid Sp is set to be substantially equal to a focal length of the objective lens 27 in the vertical direction (Z direction).

In both the configuration including the objective lens shown in FIG. 4A and the configuration including no objective lens shown in FIG. 4B, a part of the illumination light incident on the well bottom surface Wb can be regularly reflected as shown by solid line arrows in FIGS. 4A and 4B. When the spheroid Sp is present near the well bottom surface Wb, regularly reflected light from the well bottom surface Wb and reflected light from the spheroid Sp shown in broken line in FIGS. 4A and 4B are mixed with a tiny optical path length difference, whereby interference occurs. That is, the regularly reflected light from the well bottom surface Wb behaves similarly to the reference light in a pseudo manner.

Thus, as shown in FIG. 4C, the tomographic image of the imaging object obtained from the detected reflected light intensity distribution looks as if a virtual reference base surface Sv corresponding to the position of the well bottom surface Wb were present separately from an original reference base surface Sr determined by the position of the reference mirror 24. Specifically, the tomographic image is such an image that a ghost-like spheroid image Iv appearing near the virtual reference base surface Sv by the regularly reflected light is superimposed as image noise on an original spheroid image Ir appearing near the reference base surface Sr. Such image noise is one kind of so-called coherent noise and particularly called self-correlation noise in some cases.

The image noise in this case is generated because the well bottom surface Wb acts as if it were a reference mirror. Thus, the image noise is not generated if the regularly reflected light from the well bottom surface Wb is prevented from being incident on the photo-detector 26. The light regulating member 28 of this embodiment is provided to deal with this problem and has a function of partially regulating passing light.

Figure 5A:
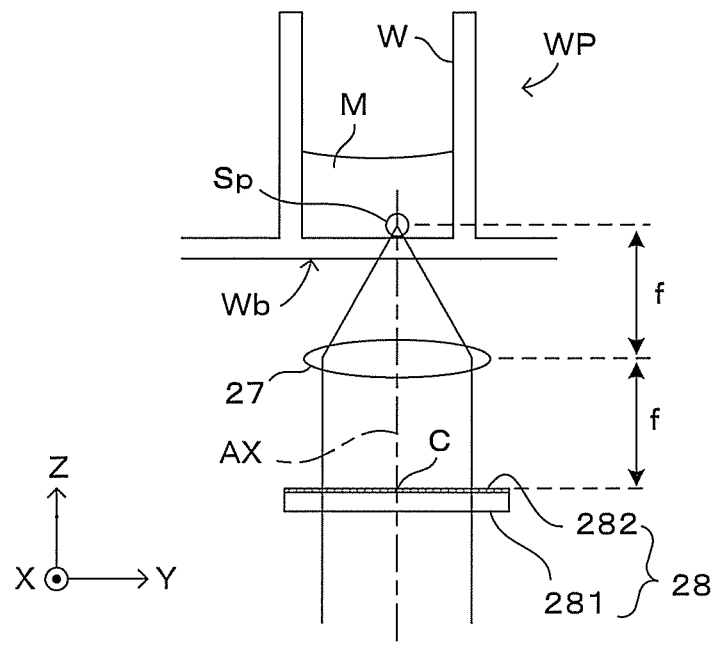
FIGS. 5A and 5B are diagrams showing the structure of the light regulating member.
Figure 5B:
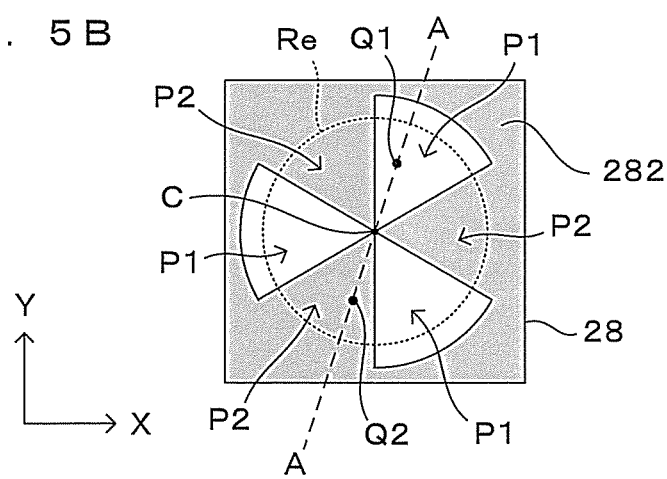
Figure 6A:
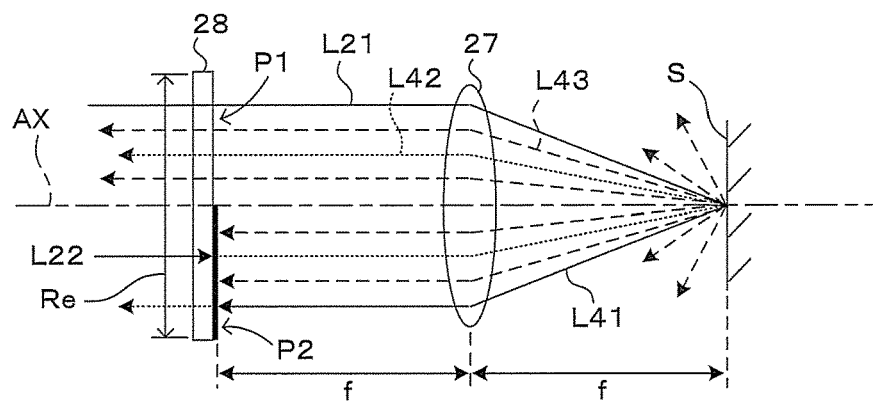
FIGS. 6A to 6C are diagrams showing the action of the light regulating member.
Figure 6B:
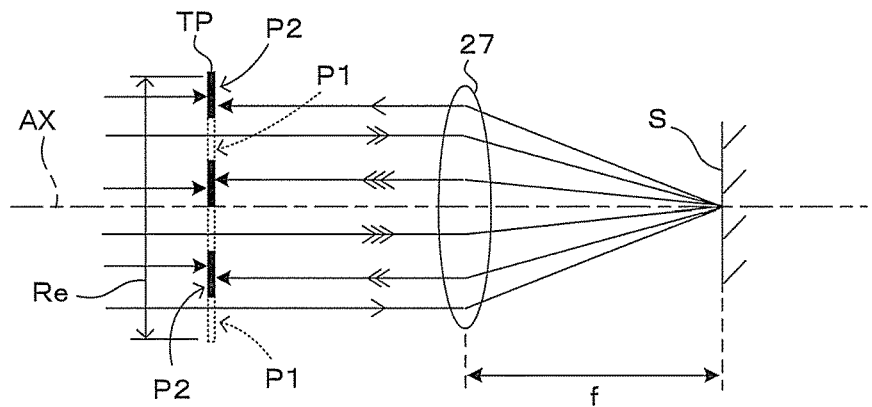
Figure 6C:
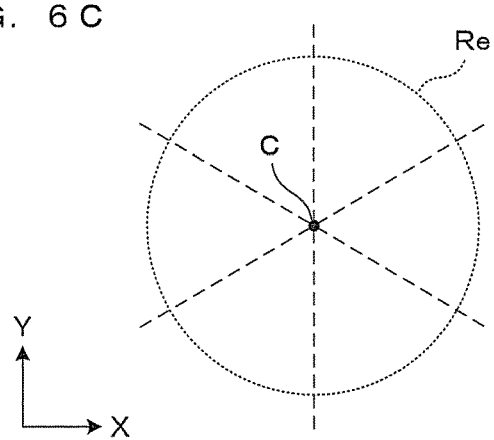

FIGS. 5A and 5B are diagrams showing the structure of the light regulating member. Further, FIGS. 6A to 6C are diagrams showing the action of the light regulating member. More specifically, FIG. 5A is a diagram showing the arrangement of the light regulating member 28 and FIG. 5B is a diagram showing a transmission pattern of the light regulating member 28. Further, FIGS. 6A and 6B are diagrams showing optical paths of light passing through the light regulating member 28 and FIG. 6C is a diagram showing an example of setting the transmission pattern. Note that a state where the orientation of the object optical system 200 is rotated by 90° is shown in FIGS. 6A and 6B.

As shown in FIGS. 5A and 5B, the light regulating member 28 is such that a light regulating film 282 having a transmission pattern in which high transmission parts P1 having a relatively high transmittance to the illumination light and low transmission parts P2 having a lower transmittance to the illumination light than the high transmission parts P1 are regularly arranged is formed on a surface of a base member 281 in the form of a flat plate transparent to the illumination light. The light regulating film 282 can be, for example, a metal deposition film. The transmittance of the high transmission parts P1 can be, for example, 100% and that of the low transmission parts P2 can be, for example, 0%. However, there is no limitation to this. Specifically, the transmittance of the high transmission parts P1 may be below 100% and that of the low transmission parts P2 may be larger than 0%. Note that the low transmission parts P2 preferably have a light absorbing property or scatters incident light to avoid adverse effects due to multiple reflection in the object optical system 200.

The light regulating member 28 is placed on a side opposite to the imaging object across the objective lens 27. For example, the light regulating member 28 can be arranged near a focus position of the objective lens 27, but may not be strictly arranged at the focus position. When the light regulating member 28 is placed at the focus position of the objective lens 27, a distance between the objective lens 27 and the light regulating member 28 is a focal length f of the objective lens 27.

The light regulating film 282 may be provided on either one of the upper surface (object side) or the lower surface (light source side) of the base member 281. The surface of the base member 281 on which the light regulating film 282 is provided functions as an effective light regulating surface for controlling the passage of light. Note that the light regulating member 28 is not limited to a combination of a base member and a light regulating film. For example, a flat plate having a light shielding property and functioning as a low transmission part may be provided with openings corresponding to high transmission parts.

The transmission pattern of the light regulating member 28 is described with reference to FIG. 5B. An area of the transmission pattern of the light regulating film 282 of the light regulating member 28 that effectively functions in regulating the passage of light is a circular area substantially centered on a point C intersecting with an optical axis AX of the objective lens 27 and having a radius equal to an effective radius of the objective lens 27 as shown in dotted line in FIG. 5B. This area is called an effective area Re below. In the effective area Re, the high transmission parts P1 and the low transmission parts P2 are arranged as follows.

The effective area Re is divided into six sector-shaped areas congruent to each other by three straight lines passing through the point C and arranged at equal angular intervals. The high transmission parts P1 and the low transmission parts P2 are alternately allocated to the six sectorial areas. Thus, one high transmission part P1 is sandwiched between two low transmission parts P2 at opposite sides, and one low transmission part P2 is sandwiched between two high transmission parts P1 at opposite sides. The entire pattern has a rotational symmetry of 120° and 240°, but does not have a rotational symmetry of 180° with the point C as a center.

Here, if a point Q2 point-symmetric with one arbitrary point Q1 included in the high transmission part P1 with respect to the point C, i.e. with the point C as a center of symmetry is considered, the point Q2 is invariably included in the low transmission part P2. Similarly, a point at a position point-symmetric with an arbitrary point in the low transmission part P2 is invariably included in the high transmission part P1.

A reason for this is described with reference to FIGS. 6A to 6C. The light regulating member 28 in FIG. 6A corresponds to a sectional view along line A-A in FIG. 5B. In the effective area Re of the light regulating film 282, a side above the optical axis AX of the objective lens 27 is the high transmission part P1 and a side therebelow is the low transmission part P2. A solid line arrow indicates an optical path of the illumination light incident from the light source located on a left side of FIG. 6A. Illumination light L21 incident on the high transmission part P1 is refracted toward the optical axis AX by the objective lens 27 and incident on a reflecting surface S near the focus position of the objective lens 27.

Regularly reflected light L41 on the reflecting surface S is emitted at a reflection angle same as an incident angle and propagates toward the light regulating member 28 via the objective lens 27. A position where this reflected light L41 is incident on the light regulating film 282 is a position point-symmetric with the incident position of the incident light L21 with respect to the point C. Thus, the regularly reflected light is incident on the low transmission part P2 of the light regulating film 282. Thus, light going to propagate toward the photo-detector (left side in FIG. 6A) beyond the light regulating member 28 is shielded by the light regulating film 282. Arrows shown by dotted lines in FIG. 6A indicate light propagation paths when the light propagates without being subjected to regulation by the light regulating film 282.

On the other hand, light L22 incident on the low transmission part P2 of the light regulating film 282 is shielded by the light regulating film 282 and not transmitted toward the objective lens 27. If the incident light L22 is transmitted through the light regulating film 282, light L42 incident on the reflecting surface S via the objective lens 27 and regularly reflected is transmitted through the high transmission part P1 of the light regulating film 282 and emitted toward the photo-detector as shown by a dotted line arrow. However, since the incident light L22 is shielded by the light regulating film 282, the emission of such regularly reflected light is not realized.

As just described, the low transmission parts P2 are provided either on the rightward optical path in FIG. 6A from the light source 21 toward the reflecting surface S or on the leftward optical path in FIG. 6A from the reflecting surface S toward the photo-detector 26 for the light incident on the reflecting surface S from the light source 21 via the object optical system 200, regularly reflected by the reflecting surface S and returning to the object optical system 200. Thus, the regularly reflected light emitted from the light regulating member 28 toward the photo-detector is largely reduced.

In contrast, scattered light L43 from the reflecting surface S is emitted in various directions as shown by broken line arrows in FIG. 6A. Thus, a part of the light is shielded by the low transmission parts P2 of the light regulating film 282 and the other part passes through the high transmission parts P1 of the light regulating film 282 and is emitted toward the photo-detector. A ratio of the shielded light out of the scattered light collected by the objective lens 27 depends on an area ratio of the high transmission parts P1 and the low transmission parts P2.

As described above, the light regulating member 28 can allow the scattered light to pass at a certain ratio while reliably attenuating the regularly reflected light from the reflecting surface S by providing the low transmission parts P2 on the optical paths thereof. When the well bottom surface Wb near the focus position of the objective lens 27 and the interface in the spheroid Sp respectively function as the reflecting surface S, the scattered light from the spheroid Sp becomes the signal light L4 to be detected, whereas the regularly reflected light from the well bottom surface Wb acts as the virtual reference light to generate image noise.

In this embodiment, a ratio of the regularly reflected light to the signal light in the light collected by the objective lens 27 and transmitted toward the photo-detector 26 via the light regulating member 28 is largely reduced and an S/N ratio in the signal light is largely improved. Specifically, it is possible to drastically reduce the generation of image noise due to the action of the regularly reflected light from the well bottom surface Wb as the virtual reference light.

FIG. 6B shows a general transmission pattern. In the example shown in FIG. 6A, the side above the optical axis AX of the objective lens 27 is the high transmission part P1 and the side therebelow is the low transmission part P2. More generally, as shown in FIG. 6B, the reflecting surface S perpendicular to the optical axis AX is virtually set at a right-side focus position of the objective lens 27 and a pattern in which the low transmission parts P2 is invariably present on optical paths of light incident from a left side of a transmission pattern TP and regularly reflected by the reflecting surface S via the objective lens 27 exhibits functions similar to the above.

Even if the transmission pattern is, for example, such that the effective area Re is equally divided into two by a single straight line passing through the point C, it is possible to prevent the regularly reflected light by the well bottom surface Wb from being incident on the photo-detector 26 as described above. However, in this case, a collection angle range of the illumination light incident on the sample and a take-in angle range of the signal light collected by the objective lens 27 and incident on the photo-detector 26 are limited. As a result, an effective NA of the optical system is reduced, leading to a reduction of resolution. To prevent such a reduction of NA, it is prerequisite that the transmission pattern of the light regulating member 28 has rotational symmetry with respect to the point C intersecting with the optical axis AX of the objective lens 27.

By the above, the transmission pattern in the effective area Re of the light regulating member 28 may be set to satisfy the following two conditions in order to reduce the image noise due to the regularly reflected light from the well bottom surface Wb without reducing the imaging resolution.

(1) The transmission pattern has rotational symmetry with respect to the point C intersecting with the optical axis AX of the objective lens 27.

(2) A point located at a position point-symmetric with one arbitrary point in the high transmission part P1 with respect to the point C is included in the low transmission part P2.

FIG. 6C shows an example of a basic setting method of the transmission pattern. As shown in FIG. 6C, the effective area Re may be divided at equal angular intervals by three or more odd number of straight lines (shown in broken line in FIG. 6C) passing through the point C and the high transmission parts P1 and the low transmission parts P2 are allocated to be alternately arranged in the respective divided sectorial areas. This makes the areas of the high transmission parts P1 and the low transmission parts P2 in the transmission pattern in the effective area Re equal, and a probability of shielding the scattered light (signal light) by the light regulating member 28 becomes 50%. If the scattered light is uniformly emitted toward the objective lens, the half of the scattered light passes through the light regulating member 28. The quantity of the scattered light passing through the light regulating member 28 while the regularly reflected light is reliably shielded is largest at this time.

On the other hand, the regularly reflected light is much more attenuated by the low transmission parts P2 and an effect of improving the S/N ratio is large. In the case of dividing the effective area Re by an even number of straight lines, high transmission parts and low transmission parts are respectively allocated at point-symmetric positions and the above effect is not obtained.

Figure 7A:
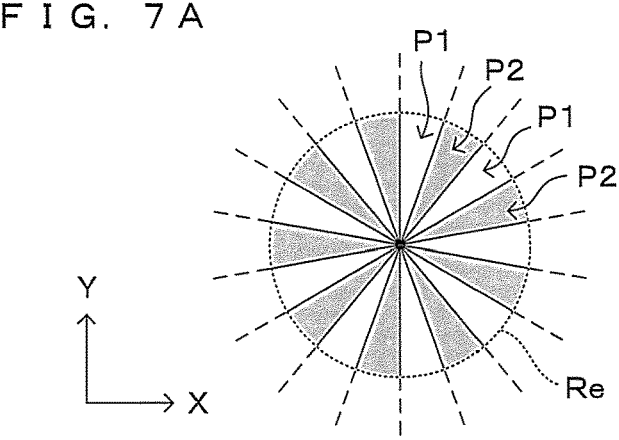
FIGS. 7A to 7C are diagrams showing other examples of the transmission pattern.
Figure 7B:
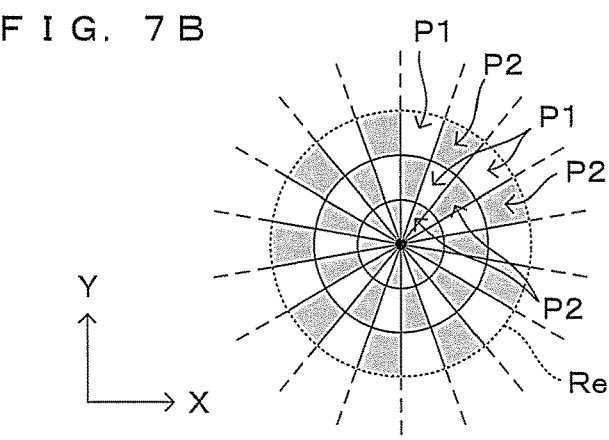
Figure 7C:
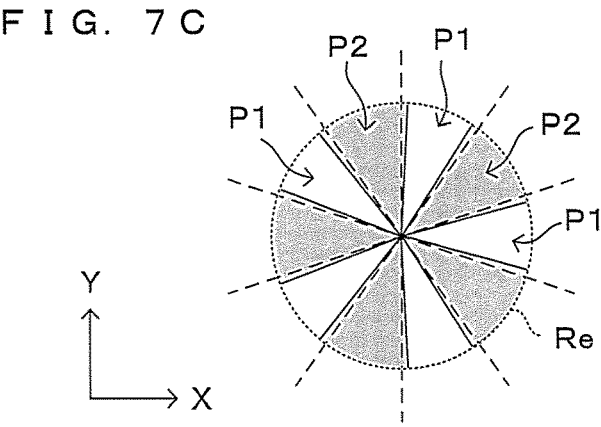

FIGS. 7A to 7C are diagrams showing other examples of the transmission pattern. The number of straight lines dividing the effective area Re is arbitrary if it is an odd number not smaller than three. In an example shown in FIG. 7A, the high transmission parts P1 and the low transmission parts P2 are alternately allocated to 18 areas equally divided by nine straight lines passing through the point C shown in broken line. Further, as shown in FIG. 7B, each of areas divided by an odd number of straight lines may be further radially divided by one or more circles centered on the point C and the high transmission parts P1 and the low transmission parts P2 may be alternately arranged in both circumferential and radial directions. Even in this case, a point located at a position point-symmetric with one arbitrary point in the high transmission part P1 with respect to the point C is included in the low transmission part P2 and the entire transmission pattern has rotational symmetry.

Further, as shown in FIG. 7C, the transmission pattern may be such that the high transmission parts P1 and the low transmission parts P2 are allocated to the respective areas divided as described above and the low transmission parts P2 slightly protrude toward the high transmission parts P1 from the boundaries of the areas. In such a transmission pattern, the low transmission parts P2 are present at positions point-symmetric with points in parts of the low transmission parts P2 with respect to the point C. That is, for the low transmission parts P2, two points located at positions point-symmetric with respect to the point C are both located in the low transmission parts P2 in some cases.

All points located at positions point-symmetric with arbitrary points in the high transmission parts P1 are included in the low transmission parts P2. Thus, the function of suppressing the incidence of the regularly reflected light by the well bottom surface on the photo-detector 26 remains to be maintained. By further increasing the area of the low transmission parts P2, the leakage of the regularly reflected light to the photo-detector 26 can be more effectively suppressed. On the other hand, the signal light is slightly more attenuated by reducing the area of the high transmission parts P1 and increasing the area of the low transmission parts P2. Such a transmission pattern may be effective in cases where the image noise due to the leakage of the regularly reflected light is particularly problematic.

In terms of most efficiently collecting the signal light, a state where the areas of the high transmission parts P1 and the low transmission parts P2 are equal is most preferable. Cases where the area of the high transmission parts P1 is increased is not preferable since the image noise increases due to the presence of optical paths along which the regularly reflected light passes through the light regulating member 28 without being attenuated by the low transmission parts P2.

Figure 8A:
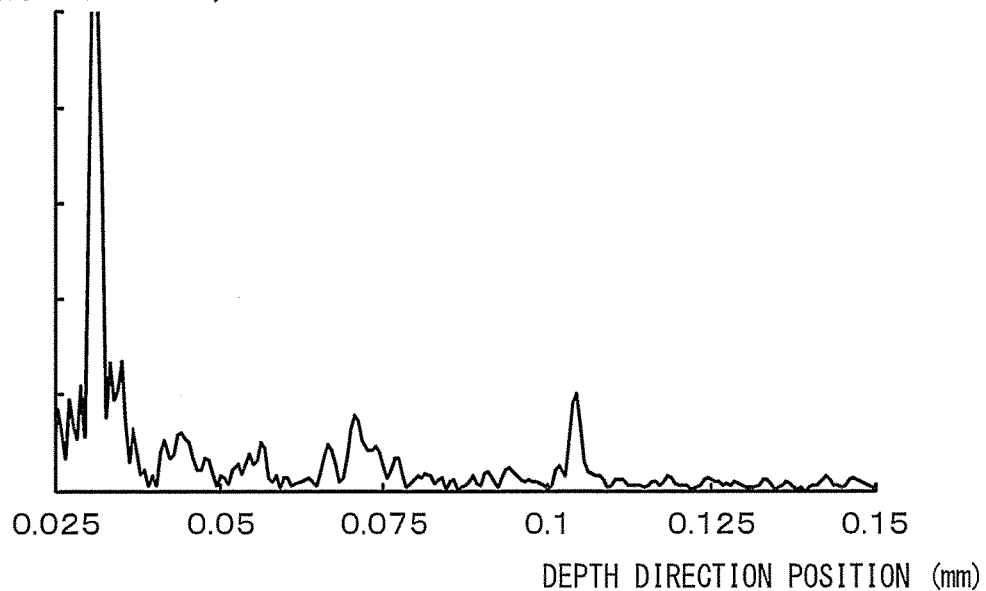
FIGS. 8A and 8B are graphs showing effects of the light regulating member.
Figure 8B:
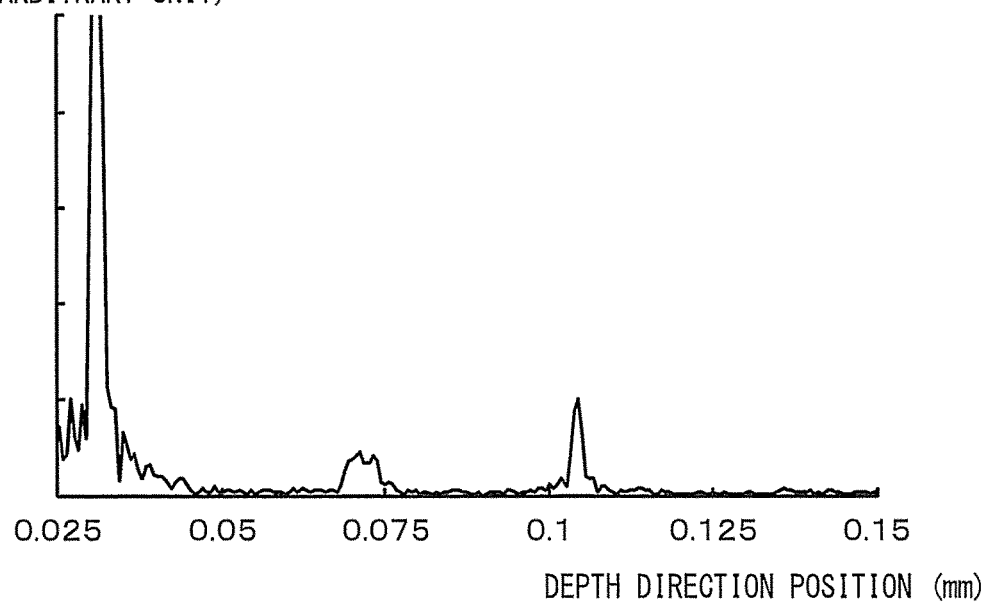

FIGS. 8A and 8B are graphs showing effects of the light regulating member. The inventors of the invention set a state where the reference light L5 was not incident on the photo-detector 26 by shielding the optical path of the reference light from the reference mirror 24 in the configuration shown in FIG. 2A and measured a distribution of reflected light intensity in a depth direction by detecting only reflected light from an appropriate imaging object. FIG. 8A shows an example in which a measurement was conducted without providing the light regulating member 28 and FIG. 8B shows an example in which a measurement was conducted with the light regulating member 28 provided. The transmission pattern shown in FIG. 7A was used.

In the case of providing no light regulating member, small peaks appear at various positions besides ghost signals due to the optical system seen near depths of 0.03 mm, 0.07 mm and 0.1 mm as shown in FIG. 8A. These small peaks are due to self-correlation signals by the imaging object. On the other hand, in the case of providing the light regulating member 28, self-correlation signals are largely reduced particularly in a depth range of 0.04 to 0.15 mm as shown in FIG. 8B, thereby showing that a ghost suppression effect is exhibited by the light regulating member 28.

As described above, in this embodiment, the light regulating member 28 is arranged on the side opposite to the imaging object across the objective lens 27 in imaging the imaging object such as a spheroid present near the bottom surface Wb of the well W via the well bottom surface Wb. The light regulating member 28 has the transmission pattern in which the high transmission parts P1 and the low transmission parts P2 are alternately and regularly arranged and selectively shields the regularly reflected light from the well bottom surface Wb while allowing the signal light (scattered light) from the imaging object to pass at a certain probability.

In this way, in this embodiment, it is possible to effectively suppress the ghost-like image noise generated by the action of the regularly reflected light as the reference light in a pseudo manner. Specifically, the signal light from the imaging object can be detected with a high S/N ratio by selectively shielding regularly reflected light from a flat surface structure such as the well bottom surface. Thus, it is possible to obtain a tomographic image representing a fine structure of an imaging object with excellent resolution particularly in imaging using a high magnification object optical system.

In this embodiment, a configuration in which the regularly reflected light from the well bottom surface Wb does not reach the photo-detector 26 while the scattered light from the imaging object is caused to be incident on the photo-detector 26 is realized by disposing the light regulating member 28 having the transmission pattern properly set. Thus, it is not necessary to open and close the optical paths of the signal light by shutters and remove regularly reflected light components from the detected light ex-post facto as with the conventional technique. Therefore, this embodiment is better than the conventional technique in simple configuration and processing speed.

Note that, as shown in FIG. 2A, the imaging unit 20 of the above embodiment is for mixing the signal light L4 and the reference light L5 to cause interference using the beam splitter 22. On the other hand, some of OCT imaging apparatuses are known to cause interference using, for example, an optical fiber coupler besides such a beam splitter as one of various optical devices capable of branching and mixing light waves. As described above, image noise can be reduced by providing a light regulating member in the thus configured device as in this embodiment.

Figure 9A:
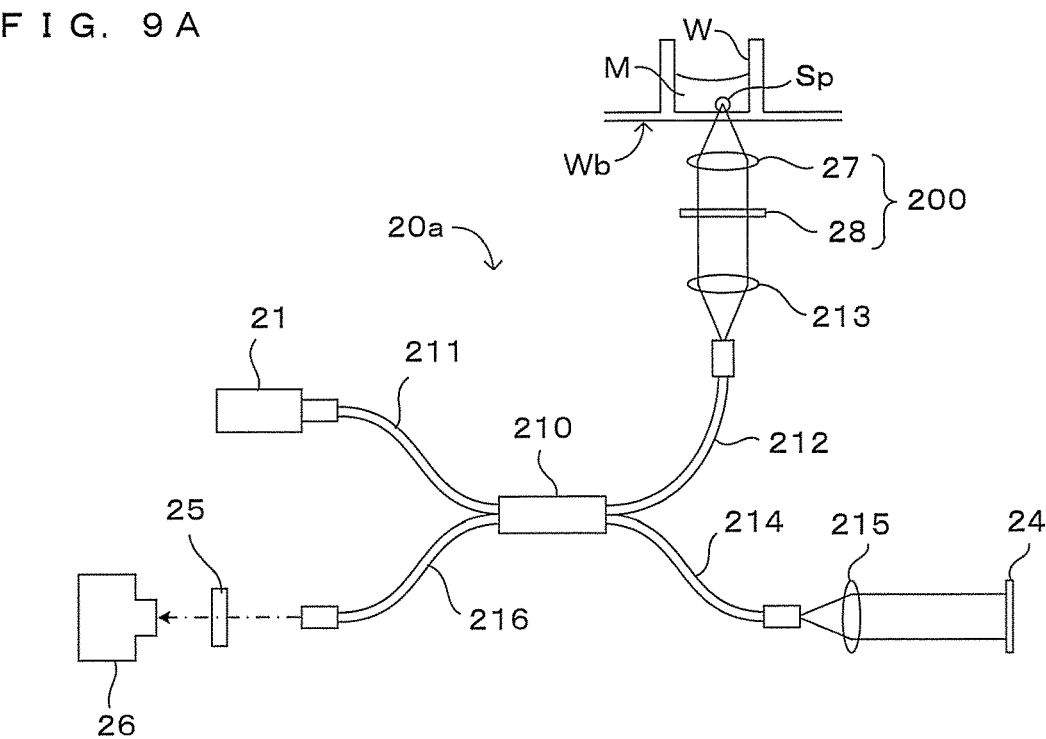
FIGS. 9A and 9B are diagrams showing other configuration examples of the OCT apparatus.
Figure 9B:
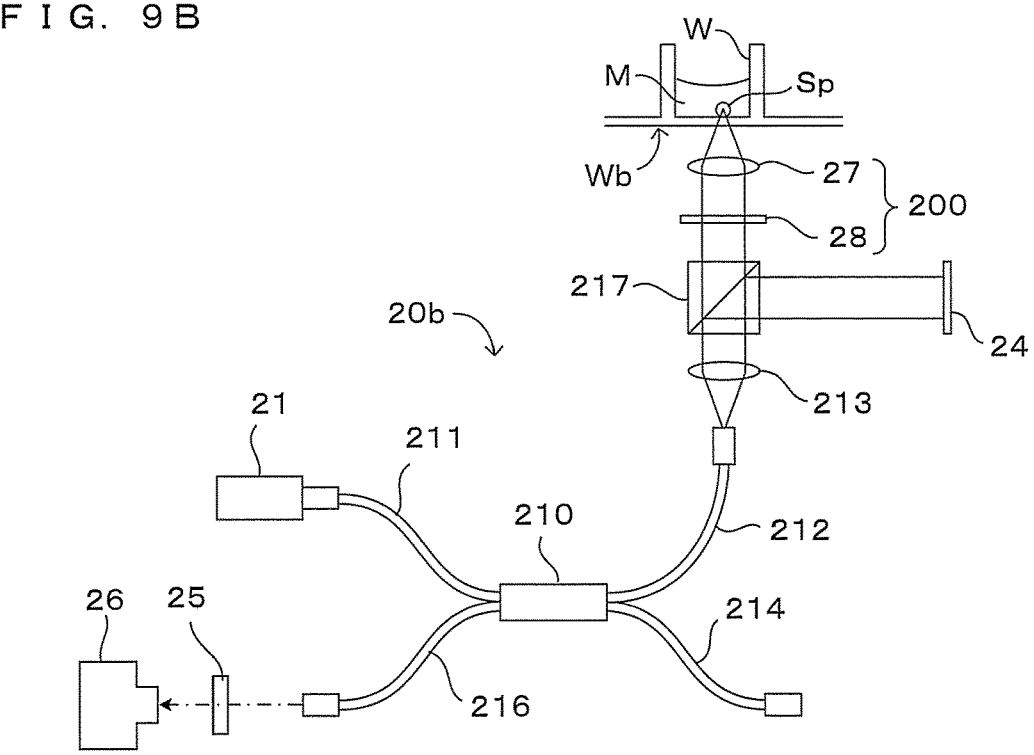

FIGS. 9A and 9B are diagrams showing other configuration examples of the OCT apparatus. Note that, in the following description, constituent components same as or corresponding to those of other embodiments are denoted by the same reference signs to facilitate understanding. The structures and functions thereof are basically the same as those of the embodiment unless particularly described, and thereby the detail description is omitted.

In an example shown in FIG. 9A, an imaging unit 20a includes an optical fiber coupler 210 instead of the beam splitter 22 as an optical device. An OCT imaging principle for detecting interference light by the optical fiber coupler is not described in detail since it is known.

One 211 of optical fibers constituting the optical fiber coupler 210 is connected to a light source 21 and low-coherence light emitted from the light source 21 is branched into lights to two optical fibers 212, 214 by the optical fiber coupler 210. The optical fiber 212 constitutes an object side optical path. More specifically, light emitted from an end part of the optical fiber 212 is incident on an object optical system 200 via a collimator lens 213. Reflected light (signal light) from an imaging object is incident on the optical fiber 212 via the object optical system 200 and the collimator lens 213.

Another optical fiber 214 constitutes a reference side optical path. More specifically, light emitted from an end part of the optical fiber 214 is incident on a reference mirror 24 via a collimator lens 215. Reflected light (reference light) from the reference mirror 24 is incident on the optical fiber 214 via the collimator lens 215. The signal light propagating in the optical fiber 212 and the reference light propagating in the optical fiber 214 interfere in the optical fiber coupler 210 and interference light is incident on a photo-detector 26 via an optical fiber 216 and a spectroscope 25. An intensity distribution of the reflected light on the imaging object is obtained from the interference light received from the photo-detector 26 as in the above embodiment.

In this example, a light regulating member 28 is arranged between the collimator lens 213 constituting the object side optical path and an objective lens 27. The configuration and functions thereof are the same as in the above embodiment. Scattered light from the imaging object is guided as the signal light to the optical fiber 212 while regularly reflected light from a well bottom surface Wb is selectively shielded.

Also in an example shown in FIG. 9B, an optical fiber coupler 210 is provided in an imaging unit 20b. However, an optical fiber 214 is not used and a collimator lens 213 and a beam splitter 217 as an optical device are provided on an optical path of light emitted from an optical fiber 212. As in the embodiment described above, an object optical system 200 and a reference mirror 24 are arranged on two optical paths branched by the beam splitter 217. In such a configuration, signal light and reference light are mixed by the beam splitter 217 and interference light generated thereby is guided to a photo-detector 26 through the optical fibers 212, 216.

Also in this example, a light regulating member 28 is arranged between the beam splitter 217 and an objective lens 27. This can suppress the incidence of regularly reflected light reflected by the well bottom surface Wb on the beam splitter 217 and only scattered light as the signal light can be guided to the photo-detector 26. As just described, also in imaging apparatuses having the configurations shown in FIGS. 9A and 9B, the generation of image noise due to the regularly reflected light from the well bottom surface Wb can be prevented by providing the light regulating member 28.

As illustrated above, the image processing apparatus 1 of the embodiment corresponds to the "imaging apparatus" of the invention for imaging the spheroid and the like as the "imaging object". Further, each of the imaging units 20, 20a, 20b functions as the "imaging unit" of the invention and the control unit 30 containing the signal processor 33 functions as the "signal processor". Further, the light regulating member 28 functions as the "light regulator" of the invention and composes the "object optical system" in conjunction with the objective lens 27. The light regulating film 282 formed on the surface of the base member 281 of the light regulating member 28 corresponds to the "light shielding surface layer". Further, the beam splitter 22 and the optical fiber coupler 210 function as the "optical device". The reference mirror 24 and the photo-detector 26 function as the "reflector" and the "photo-detector" of the invention respectively.

Note that the invention is not limited to the above embodiments and various changes other than those described above can be made without departing from the gist of the invention. For example, the light regulating member 28 in the above embodiments is such that the light regulating film 282 having a light shielding property is formed on one surface of the base member 281 in the form of a flat plate having optical transparency. However, a "light regulator" of the invention is not limited to such a configuration. For example, as described above, openings as the high transmission parts P1 may be provided in a flat plate member having a light shielding property as the low transmission part P2. Further, the light regulator is not limited to a flat plate shape and a part of a member having a more complicated shape may have a flat surface part functioning as the "light regulator" of the invention. Further, one surface facing the objective lens out of wall surfaces of a tubular body for supporting the objective lens may function as a light regulating surface.

Further, the above embodiment is a so-called Fourier domain OCT imaging apparatus for obtaining the reflected light intensity distribution in the depth direction from intensity of interference at each wavelength using illumination light including wavelength components in a wide range. However, besides this, the invention can be applied to various imaging apparatuses for tomographic imaging using the OCT imaging principle such as a time domain OCT imaging apparatus.

Further, a general-purpose processing device having a general configuration such as a personal computer or a work station can also be used as the control unit 30 of the above embodiment. Specifically, the image processing apparatus 1 may be configured by a combination of the imaging unit 20, the scan drive mechanism 40, the imaging device having minimum control functions for operating the imaging unit 20 and the scan drive mechanism 40 and a personal computer or the like functioning as the control unit 30 by executing a control program describing the above processing contents.

As described by way of the specific embodiment, in the present invention, the transmission pattern may be, for example, a pattern in which the high transmission part and the low transmission part are alternately allocated to a plurality of sector-shaped areas formed by dividing a circle centered on one point by three or more odd number of straight lines intersecting at the one point and arranged at equal angular intervals. The transmission pattern set in this way satisfies the conditions for selectively regulating the regularly reflected light and can ensure a high S/N ratio between the scattered light from the imaging object as the signal light and the regularly reflected light while preventing a reduction of resolution due to a reduction of the effective numerical aperture.

Further, for example, a point located at a position point-symmetric with an arbitrary point in the low transmission part with respect to a point through which the optical axis of the objective lens passes may be included in the high transmission part on the light regulating surface. For the purpose of reliably regulating the passage of the regularly reflected light, at least points located at positions point-symmetric with points in the high transmission part have only to be located in the low transmission part. In this respect, points located at positions point-symmetric with points in the low transmission part may be located in the low transmission part. However, an increase in the area of the low transmission part is equivalent to an increase in the area where the signal light is shielded, and the quantity of the detected signal light is reduced. To set a point located at a position point-symmetric with an arbitrary point in the high transmission part in the low transmission part and set a point located at a position point-symmetric with an arbitrary point in the low transmission part in the high transmission part means nothing but making the areas of the high transmission part and the low transmission part equal in an area effectively functioning as the light regulating surface. At this time, the quantity of the signal light passing through the light regulating surface can be maximized.

Further, for example, the low transmission part may have a light absorbing or scattering property. According to such a configuration, it can be suppressed that light reflected by the low transmission part becomes stray light to generate image noise.

Further, for example, the light regulating surface may be arranged at a focus position of the objective lens. According to such a configuration, it is possible to obtain effects similar to those of an object-side telecentric optical system having an aperture stop provided at a focus position, i.e. such a property that the size of an image does not change even if the position of the imaging object changes in the depth direction.

Further, for example, the light regulator may be such that an opening as the high transmission part is partially provided on a flat plate having a light shielding property. Alternatively, the light regulator may be such that a light shielding surface layer as the low transmission part is partially formed on a flat surface having optical transparency. It is possible to selectively regulate the regularly reflected light as a noise source while allowing the passage of the scattered light as the signal light by either configuration.

Further, for example, the objective lens may be arranged such that the optical axis is perpendicular to the wall surface. It is also considered to incline the optical axis of the objective lens with respect to the wall surface as a configuration for preventing the regularly reflected light from being incident on a detector. However, particularly in the case of using an optical system having a large NA in high magnification imaging, the optical axis has to be largely inclined to completely shield the regularly reflected light, which is not realistic. Even in such a case, by applying the configuration of the invention, the regularly reflected light can be regulated by the light regulator without inclining the optical axis and reducing the NA of the optical system and the generation of image noise can be suppressed.

Further, for example, the light source may emit light having a plurality of wavelength components and the detector may spectrally diffract interference light and output a light intensity of each wavelength component as an interference signal. According to such a configuration, the reflected light intensity distribution in the depth direction can be obtained without mechanically changing the optical path length of the reference light, utilizing such a property that the depth of the reflecting surface where interference occurs differs depending on wavelength. Thus, a tomographic image can be obtained in a short processing time.

Further, the detector can include, for example, an optical device which has a function of dividing light from the light source into a plurality of branch lights and a function of mixing the signal light and the reference light, a reflector which reflects one branch light emitted from the optical device and serving as the reference light toward the optical device, thereby specifies an optical path length of the reference light, and a photo-detector which receives mixed light of the signal light and the reference light emitted from the optical device and outputs the interference signal. The imaging apparatus including the detector having such a configuration is known as an OCT imaging apparatus and is suitably applicable for the purpose of obtaining a tomographic image.

This invention can be applied to OCT imaging techniques in general. Particularly, this invention can be suitably applied in the fields of medicine, biochemistry and drug discovery for imaging cells and cell clusters cultured in a container such as a well plate.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

What is claimed is:

1. An imaging apparatus for tomographically imaging an imaging object carried in a carrier having an optically transparent wall surface, the imaging apparatus comprising:
    a light source which emits low-coherence light to be split into illumination light and reference light, the illumination light being incident on the imaging object via an object optical system and reflected by the imaging object, reflected light from the imaging object passing through the object optical system;
    an imaging unit which detects interference light generated by an interference of the reflected light and the reference light, and outputs an interference signal corresponding to the interference light; and
    a signal processor which obtains a reflected light intensity distribution of the imaging object along an incident direction of the illumination light based on the interference signal, wherein
    the object optical system includes an objective lens and a light regulator,
    the objective lens is arranged to face the wall surface, converges the illumination light to the imaging object via the wall surface and collects the reflected light from the imaging object emitted via the wall surface,
    the light regulator is arranged on an optical path of the illumination light on a side opposite to the imaging object across the objective lens and has a light regulating surface formed with a transmission pattern in which a high transmission part for transmitting the illumination light at a relatively high transmittance and a low transmission part having a lower transmittance to the illumination light than the high transmission part are regularly arranged,
    the transmission pattern is rotationally symmetric with respect to an optical axis of the objective lens and a point located at a position point-symmetric with an arbitrary point in the high transmission part with respect to a point where the optical axis of the objective lens intersects with the light regulating surface is included in the low transmission part, and
    the light regulating surface is arranged at a focus position of the objective lens.

2. The imaging apparatus according to claim 1, wherein the transmission pattern is a pattern in which the high transmission part and the low transmission part are alternately allocated to a plurality of sector-shaped areas formed by dividing a circle centered on one point by three or more odd number of straight lines intersecting at the one point and arranged at equal angular intervals.

3. The imaging apparatus according to claim 1, wherein a point located at a position point-symmetric with an arbitrary point in the low transmission part with respect to a point through which the optical axis of the objective lens passes is included in the high transmission part on the light regulating surface.

4. The imaging apparatus according to claim 1, wherein an area of the high transmission part and an area of the low transmission part are equal in an area effectively functioning as the light regulating surface.

5. The imaging apparatus according to claim 1, wherein the low transmission part has a light absorbing or scattering property.

6. The imaging apparatus according to claim 1, wherein the light regulator includes a flat plate which has a light shielding property and on which an opening as the high transmission part is partially provided.

7. The imaging apparatus according to claim 1, wherein the light regulator includes a flat plate which has optical transparency and on which light shielding surface layer as the low transmission part is partially formed.

8. The imaging apparatus according to claim 1, wherein the objective lens is arranged such that the optical axis is perpendicular to the wall surface.

9. The imaging apparatus according to claim 1, wherein
    the light source emits light having a plurality of wavelength components and
    the imaging unit spectrally diffracts the interference light and outputs a light intensity of each wavelength component as the interference signal.

10. The imaging apparatus according to claim 1, wherein the imaging unit includes:

an optical device which has a function of dividing light from the light source into a plurality of branch lights and a function of mixing the reflected light and the reference light, one of the branch lights being the illumination light;

a reflector which reflects another branch light from the optical device toward the optical device, the reflected another branch light serving as the reference light, the reflector being positioned so that an optical path length of the reference light is approximately equivalent to an optical path length of the reflected light from the imaging object; and a photo-detector which receives mixed light of the reflected light and the reference light emitted from the optical device and outputs the interference signal.

11. An imaging method for tomographically imaging an imaging object carried in a carrier having an optically transparent wall surface, the imaging method comprising:

dividing low-coherence light emitted from a light source into illumination light and reference light, the illumination light being incident on the imaging object via an object optical system and reflected by the imaging object, reflected light from the imaging object passing through the object optical system;

detecting interference light generated by an interference of the reflected light and the reference light; and obtaining a reflected light intensity distribution of the imaging object along an incident direction of the illumination light based on the detected interference light, wherein the object optical system includes an objective lens and a light regulator, the objective lens is arranged to face the wall surface, converges the illumination light to the imaging object via the wall surface and collects the reflected light from the imaging object emitted via the wall surface, the light regulator is arranged on an optical path of the illumination light on a side opposite to the imaging object across the objective lens and has a light regulating surface formed with a transmission pattern in which a high transmission part for transmitting the illumination light at a relatively high transmittance and a low transmission part having a lower transmittance to the illumination light than the high transmission part are regularly arranged, the transmission pattern is rotationally symmetric with respect to an optical axis of the objective lens and a point located at a position point-symmetric with an arbitrary point in the high transmission part with respect to a point where the optical axis of the objective lens intersects with the light regulating surface is included in the low transmission part, and the light regulating surface is arranged at a focus position of the objective lens.

* * * * *